(12) United States Patent
Liao

(10) Patent No.: US 12,226,144 B1
(45) Date of Patent: Feb. 18, 2025

(54) OVERMOLDED ELECTROCAUTERY DISSECTING DEVICES AND SYSTEMS HAVING A GAS DELIVERY ASSEMBLY

(71) Applicant: MODULE MED LLC, Sugar Land, TX (US)

(72) Inventor: Kevin Zhenmei Liao, Sugar Land, TX (US)

(73) Assignee: MODULE MED LLC, Sugar Land, TX (US)

( * ) Notice: Subject to any disclaimer, the term of this patent is extended or adjusted under 35 U.S.C. 154(b) by 0 days.

(21) Appl. No.: 18/644,578

(22) Filed: Apr. 24, 2024

Related U.S. Application Data

(60) Provisional application No. 63/607,459, filed on Dec. 7, 2023.

(51) Int. Cl.
*A61B 18/14* (2006.01)
*A61B 18/00* (2006.01)

(52) U.S. Cl.
CPC .... *A61B 18/14* (2013.01); *A61B 2018/00077* (2013.01); *A61B 2018/00083* (2013.01); *A61B 2018/00136* (2013.01); *A61B 2018/00172* (2013.01); *A61B 2018/00595* (2013.01); *A61B 2018/00702* (2013.01); *A61B 2018/0072* (2013.01); *A61B 2018/00922* (2013.01); *A61B 2018/0097* (2013.01); *A61B 2018/1412* (2013.01); *A61B 2218/005* (2013.01)

(58) Field of Classification Search
CPC .................. A61B 18/14; A61B 18/042; A61B 2018/00577; A61B 2018/00589; A61B 2018/00601; A61B 2018/1213; A61B 2018/1412; A61B 2018/00077; A61B 2018/00083; A61B 2018/00136; A61B 2018/00172; A61B 2018/00595; A61B 2018/00702; A61B 2018/0072; A61B 2018/0091; A61B 2018/00922; A61B 2018/0097; A61B 2218/005
USPC ...................................... 606/45–50
See application file for complete search history.

(56) References Cited

U.S. PATENT DOCUMENTS 3,906,955 A 9/1975 Roberts
4,781,175 A 11/1988 McGreevy
(Continued)

OTHER PUBLICATIONS

Gilbert, Shegu et al., "Modified carbodissection: A new technique for harvesting the internal mammary artery", Surg. Oct. 29, 2017;2017. doi: 10.1510/mmcts.2017.018. PMID: 29300076, 1 page.
(Continued)

*Primary Examiner* — Michael F Peffley
(74) *Attorney, Agent, or Firm* — Moore & Van Allen PLLC

(57) ABSTRACT

An electrocautery device for dissecting biological tissue is provided. The electrocautery device includes an insulated electrode comprising a distal tip configured to provide energy to biological tissue and an electrocautery device body having a lower portion and an upper portion. The lower portion is radially disposed upon the insulated electrode. The upper portion comprising a proximal first portion comprising a gas supply connection and a distal second portion defining a gas delivery channel and having a gas tip. The electrocautery device may optionally include a buffer. Systems for dissecting biological tissue are also provided.

20 Claims, 6 Drawing Sheets

(56) References Cited

U.S. PATENT DOCUMENTS

| | | | |
|---|---|---|---|
| 5,088,997 A * | 2/1992 | Delahuerga | A61B 18/042 606/49 |
| 5,154,709 A | 10/1992 | Johnson | |
| 5,720,745 A * | 2/1998 | Farin | A61B 18/042 606/49 |
| 6,090,106 A | 7/2000 | Goble | |
| 6,602,249 B1 * | 8/2003 | Stoddard | A61B 18/14 606/41 |
| 7,235,071 B2 * | 6/2007 | Gonnering | A61B 18/042 604/35 |
| 8,057,470 B2 | 11/2011 | Lee | |
| 8,906,048 B2 | 12/2014 | Lin | |
| 10,792,086 B2 | 10/2020 | Trivedi | |
| 11,291,492 B2 | 4/2022 | Trivedi | |
| 2004/0044342 A1 | 3/2004 | Mackay | |
| 2004/0138658 A1 | 7/2004 | Farin | |
| 2005/0080408 A1 * | 4/2005 | Seid | A61B 18/1402 606/49 |
| 2006/0069387 A1 | 3/2006 | Gedebou | |
| 2011/0077645 A1 | 3/2011 | Lin | |
| 2016/0128757 A1 | 5/2016 | Trivedi | |
| 2019/0216485 A1 | 7/2019 | Aljuri | |
| 2021/0007787 A1 | 1/2021 | Canady | |

OTHER PUBLICATIONS

Samuels, Jason M. et al., "Carbon dioxide can eliminate operating room fires from alcohol-based surgical skin preps", National Library of Medicine, Surg Endosc. Apr. 2020;34(4):1863-1867, doi: 10.1007/s00464-019-06939-z. Epub Jun. 20, 2019. PMID: 31222632, 1 page.

* cited by examiner

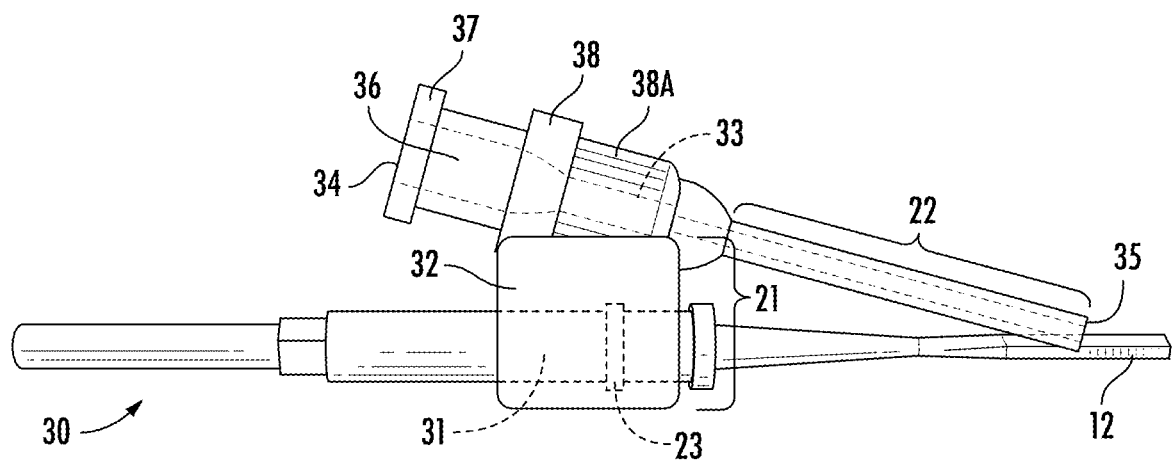
FIG. 2
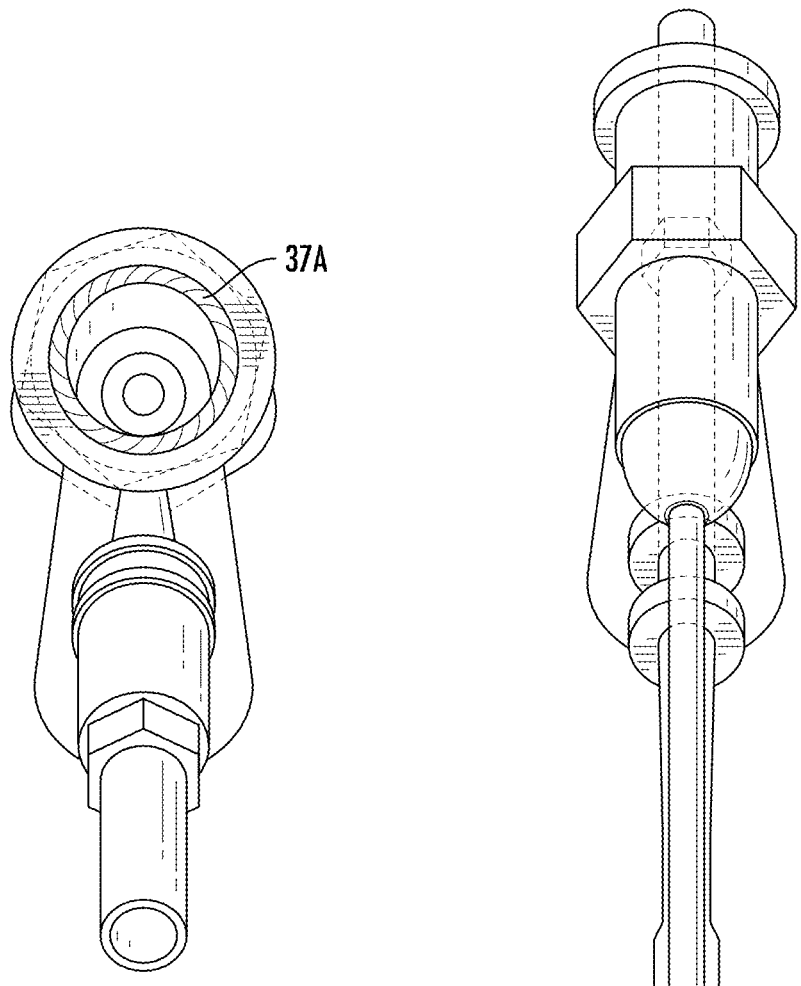
FIG. 3
FIG. 4

OVERMOLDED ELECTROCAUTERY DISSECTING DEVICES AND SYSTEMS HAVING A GAS DELIVERY ASSEMBLY

CROSS-REFERENCE TO RELATED APPLICATIONS

This application claims the benefit of U.S. Provisional Patent Application. No. 63/607,459, filed Dec. 7, 2023, the entirety of which is incorporated herein by reference.

FIELD

The present invention relates to electrocautery devices for and systems for dissecting biological tissue. The devices and methods are generally applicable in healthcare settings and, more particularly, in surgical settings.

BACKGROUND

Electrocautery devices are used to dissect, cut, coagulate, desiccate, and/or fulgurate biological tissue by applying an electric current to the tissue via an electrocautery tip on the device. Electrocautery devices may be operated using a cautery handpiece which, when connected to an energy source (such as an electrical generator), allow a user to selectively vary the amount of power provided to the electrocautery device from the energy source, thereby facilitating controlled dissection of tissue. Electrocautery devices currently known in the art are not reliably safe when used near fragile and important structures such as vessels and nerves.

During surgical operations, known electrocautery tips can cause vessels to become injured during cutting and dissecting in the tissue if the tip is touching the vessel directly or in too close of proximity to the vessels. Additionally, the effectiveness of existing electrocautery devices can be adversely affected by factors such as pooled body fluid (e.g., blood) in the surgical field and char build-up on the electrocautery tip. Further, known electrocautery devices generate smoke which can reduce visibility in a surgical setting and have the potential to cause fires in high-oxygen operative fields such as the head, neck, and chest areas where oxygen is delivered to a patient.

Accordingly, there is a need for electrocautery devices and methods of use that can be safely and effectively used around fluids, do not cause tissue injury, and mitigate fire risks.

BRIEF SUMMARY

In a first aspect, an electrocautery device for dissecting biological tissue is provided. The electrocautery device comprises an insulated electrode and an electrocautery device body. The insulated electrode of the electrocautery device comprises an electrode having a distal tip configured to deliver an electrical current to a biological tissue and a proximal end configured to be coupled to an energy supply source and an insulation material radially disposed on only a middle portion of the electrode such that the distal tip and the proximal end of the electrode is not covered by the insulation material. The electrocautery device body of the electrocautery device is formed from a device body material and comprises a lower portion radially disposed upon the insulated electrode and an upper portion formed as a single unitary piece with the lower portion. The upper portion defines a gas delivery assembly comprising a first portion formed at the proximal end of the upper portion and a second portion formed at the distal end of the upper portion and adjacent to the first portion. The first portion of the upper portion comprises a gas supply connection that is configured to be coupled to a gas supply source. The second portion defines a gas delivery channel having a gas tip, wherein the gas delivery channel is in fluid communication with the gas supply connection such that, when a gas supply source is coupled to the gas supply connection, the gas delivery channel is configured to deliver a gas provided by the gas supply source to a biological tissue via the gas tip.

In some embodiments, the insulated electrode is formed by overmolding the insulation material onto a middle portion of the electrode. In some such embodiments, the insulation material may be overmolded onto a middle portion of the electrode by injection molding. In certain embodiments, the electrocautery device body is formed by overmolding the device body material onto the insulated electrode. In some such embodiments, the insulation material is overmolded onto a middle portion of the electrode by injection molding. In some embodiments, the insulation material is overmolded onto a middle portion of electrode by compression molding.

In some embodiments, the distal tip of the electrode is shaped as a blade. In some embodiments, the gas tip is formed from a third material that is distinct from the insulation material and the device body material. In certain embodiments, the gas tip is disposed adjacent to the distal tip of the insulated electrode. The gas tip may contact the distal tip at least one location to facilitate preferred gas dispersion patterns.

In some embodiments, the gas supply connection is a threaded connection. Additionally or alternatively, the gas supply connection may be a tapered connection configured to facilitate a friction fit between the gas supply source and the gas supply connection.

In some embodiments, the insulated electrode further comprises a buffer disposed on an external surface of the insulation material and configured to mitigate or prevent deformation of the insulation material. In such embodiments, the buffer may optionally comprise one or more lugs on at least one end of the buffer and the insulation material comprises anti-rotation tabs. In such embodiments the lugs and the anti-rotation tabs are configured to interact such that the buffer is held in place by the anti-rotation tabs.

In some embodiments, the proximal end of the electrode is configured to be coupled to a handpiece that is operably coupled to the energy supply source and configured to, when manipulated by a user, increase or decrease an amount of power provided to the electrocautery device by the electrical current.

In some embodiments, the second portion of the upper portion of the electrocautery device body and the lower portion of the electrocautery device body form an acute angle. In some embodiments, the second portion of the upper portion of the electrocautery device body and the lower portion of the electrocautery device body is canted such that the angle between its proximal end and the lower portion of the device body is less than the angle between its distal end and the lower portion of the device body. In other embodiments, the second portion of the upper portion of the electrocautery device body and the lower portion of the electrocautery device body is canted such that the angle between its proximal end and the lower portion of the device body is greater than the angle between its distal end and the lower portion of the device body.

In a second aspect, a system for dissecting biological tissue is provided. The system comprises an electrocautery device, a gas supply source coupled to a gas supply of the electrocautery device via a gas supply tube, an energy supply source configured to deliver an electrical current to the electrode of the electrocautery device, and a handpiece that is operably coupled to the energy supply source. In some embodiments, the gas supply tube is permanently coupled to the gas supply connection of the electrocautery device via overmolding.

The electrocautery device of the system for dissecting biological tissue comprises an insulated electrode and an electrocautery device body. The insulated electrode of the electrocautery device comprises an electrode having distal tip configured to deliver an electrical current to a biological tissue and a proximal end configured to be coupled to an energy supply source and an insulation material radially disposed on only a middle portion of the electrode such that the distal tip and the proximal end of the electrode is not covered by the insulation material. The electrocautery device body of the electrocautery device is formed from a device body material and comprises a lower portion radially disposed upon the insulated electrode and an upper portion formed as a single unitary piece with the lower portion. The upper portion defines a gas delivery assembly comprising a first portion formed at the proximal end of the upper portion and a second portion formed at the distal end of the upper portion and adjacent to the first portion. The first portion of the upper portion comprises a gas supply connection that is configured to be coupled to a gas supply source. The second portion defines a gas delivery channel having a gas tip, wherein the gas delivery channel is in fluid communication with the gas supply connection such that, when a gas supply source is coupled to the gas supply connection, the gas delivery channel is configured to deliver a gas provided by the gas supply source to a biological tissue via the gas tip.

In some embodiments, the system further comprises a gas pump operably coupled to a proximal end of the gas tube and configured to facilitate movement of a gas from the gas source to the gas delivery assembly of the electrocautery device. In some such embodiments, the gas tube is secured to the wire of the handpiece via a coupler.

BRIEF DESCRIPTION OF THE SEVERAL VIEWS OF THE DRAWING(S)

In order to understand and to see how the present disclosure may be carried out in practice, examples will now be described, by way of non-limiting examples only, with reference to the accompanying drawings, in which:

FIG. 2 illustrates an example of the electrocautery device.

FIG. 3 illustrates an additional view of the electrocautery device of FIG. 2.

FIG. 4 illustrates another additional view of the electrocautery device of FIG. 2.

DETAILED DESCRIPTION

The invention now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

Definitions

As used herein, the terms "coupled" and "operably coupled" may refer to one or more components being electrically, mechanically, thermally, chemically, or otherwise linked to another component(s). For example, components may be part of the same structure and/or integral with one another (i.e., "directly coupled"). In other examples, components may be connected via remote means (e.g., via a signal transmitted to an electronic circuit).

As used herein, the term "dissect" (and all of its derivative forms) may refer to dissecting, cutting, desiccating, and/or fulgurating tissue as well as the coagulation of biological fluids.

As used herein, the term "overmold" (and all of its derivative forms) may refer to any process by which a material is molded over a base substrate, such as, by way of non-limiting example, compression molding or injection molding.

The present invention is an electrocautery device comprising a low-profile gas delivery assembly configured to simultaneously deliver a gas while dissecting biological tissue, thereby reducing the generation of smoke and potential fire hazard by reducing oxygen concentrations in the surgical area, keeping the operative field dry, clearing debris, and increasing visibility of the surgical site.

The electrocautery device is constructed by coating the middle portion of an electrode with an insulation material to form an insulated electrode. The distal tip of the electrode remains exposed for contacting tissue and the proximal end of the electrode is exposed for attachment to an electrosurgical handpiece. The insulated electrode is then overmolded with a device body material to form an electrocautery device body. Optionally, a buffer may be added between the insulation material and the device body material to prevent deformation of the insulation material during the overmolding process.

Figure 1A:
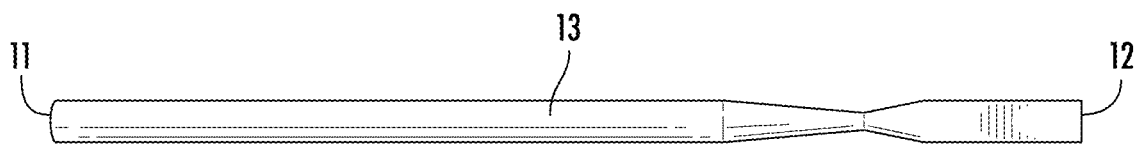
FIG. 1A illustrates an electrode for use in an electrocautery device.

With reference to FIG. 1A, an electrode 13 is illustrated. The electrode 13 comprises a distal tip 12 configured to deliver an electrical current to biological tissue and a proximal end 11 configured to be coupled to an energy source. The proximal end 11 of the electrode 13 may be sized and designed such that it may be operably coupled with an electrosurgical handpiece provided by a variety of different manufacturers. In some embodiments, the distal tip 12 is shaped in a manner conducive to cutting tissue such as in a blade shape. The length of the electrode 13 may vary depending on type of desired operation.

The electrode 13 is comprised of an electrically conductive material such as a metal or metal alloy. In certain embodiments, the electrode 13 is comprised of a stainless steel, such as 304 stainless steel. In some such embodiments, the electrode 13 consists of a stainless steel, such as 304 stainless steel. In order to facilitate improved self-cleaning capabilities, the distal tip 12 may be coated with a polymer layer, such as a PTFE layer.

In some embodiments, the electrode 13 may be and/or include a monopolar blade electrode, a bipolar electrode, and/or the like. Additionally, or alternatively, the electrode 13 may be and/or include a plurality of electrodes.

Figure 1B:
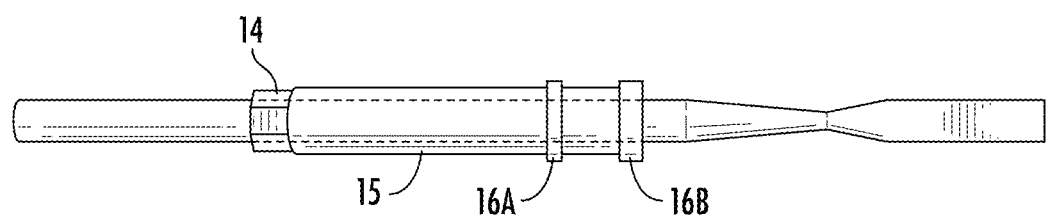
FIG. 1B illustrates an electrode having a layer of insulating material disposed thereon.
Figure 1C:
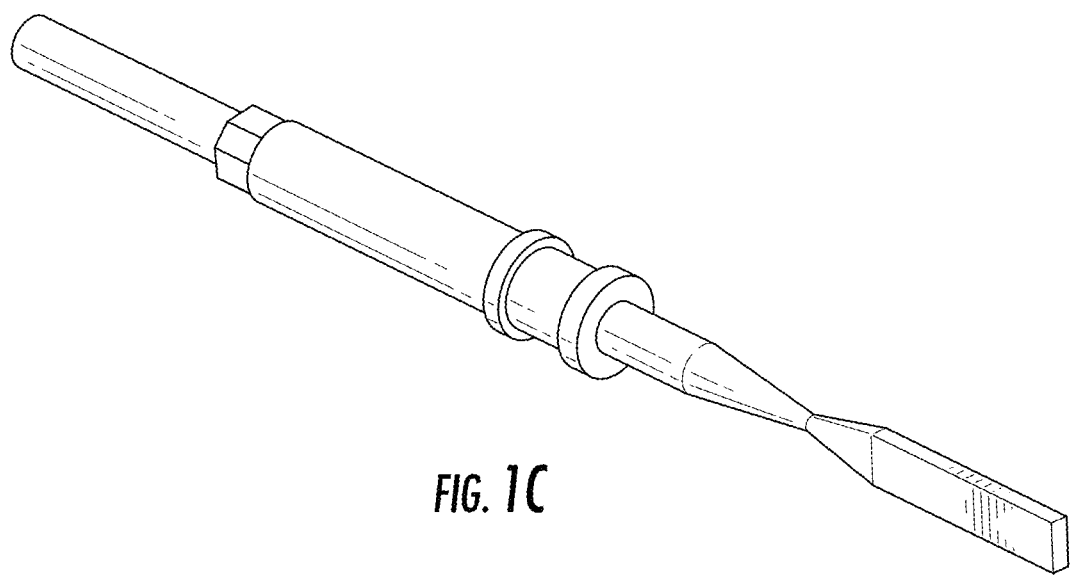
FIG. 1C illustrates an isometric view of the insulated electrode of FIG. 1B.

With reference to FIGS. 1B and 1C, the electrode 13 is illustrated with a layer of insulation material 14 radially disposed on a middle portion of the electrode. The insulation material 14 is overmolded onto the electrode to form a body 15, which is shaped cylindrically to avoid snagging. The proximal end of the insulation material 14 is formed into a hexagonal shape in order to facilitate coupling with an electrosurgical handpiece. The distal tip 12 and proximal end 11 of the electrode are exposed (i.e., not covered by the insulation material).

The insulation material may be selected from materials having a relatively low dielectric constant, as compared to the device body material and the material comprising the electrode. In some embodiments, the insulation material comprises a polymer. In some such embodiments, the insulation material comprises PTFE.

In various embodiments, additional texturing of the insulation 16A and 16B can be added to improve the connection between the insulated electrode (e.g., formed by the electrode 13 and the insulation material 14) and the electrocautery device body 32 (shown in FIG. 2) by improving the traction between the material forming the electrocautery device body and the insulating body. Texturing also assists the user in gripping the electrocautery device during tissue dissection.

With reference to FIGS. 2-4, an electrocautery device 30 is illustrated. The electrocautery device comprises an insulated electrode 31 and an electrocautery device body 32 having both a lower portion 21 that is radially disposed around the insulated electrode 31 and an upper portion 33 which is formed as a single unitary piece with the lower portion.

The upper portion 33 of the electrocautery device body comprises a first portion 34 at its proximal end and a second portion 22 at its distal end. The first portion 34 comprises a gas supply connection 37 that is couplable to a gas supply source. The gas supply source may be coupled to the gas supply connection directly or, alternatively, via a gas supply tube. In some embodiments, the gas supply connection includes threading 37A to accommodate gas supply sources that may be coupled via the threaded adapters of the gas supply connection. In some such embodiments (as depicted in FIG. 3), the threading is on an interior surface of the gas supply connection. Additionally or alternatively, the threading may be on an exterior surface of the gas supply connection. In some embodiments, the gas supply connection is tapered to create a friction-fit with a gas supply source, such as in a Luer Taper.

In some embodiments, the electrocautery device further comprises the gas tube and/or gas source. In such embodiments, the gas tube is permanently coupled to the gas supply connection of the electrocautery device via overmolding. For example, one or more materials may be overmolded over at least a portion of the overlapping sections of the gas tube and the gas supply connection. Alternatively, the gas tube may be permanently coupled to the electrocautery device by overmolding the gas tube with the device body material defining the gas supply connection. This connection may be formed at the time the electrocautery device body is initially formed.

The second portion 22 is formed at the distal end of the upper portion and adjacent to the first portion. The second portion defines a gas delivery channel having a gas tip 35 on its distal end. The gas tip is placed tangent to a flat side of the blade and rearward from the blade's distal tip to minimize the chance of blockage. The gas delivery channel 36 is in fluid communication with the gas supply connection 37 such that, when the electrocautery device is in use, gas flows through the gas delivery channel without obstruction and is delivered to the tissue adjacent the distal end of the electrocautery device. The second portion 22 is angled at its distal end. In some embodiments, the second portion is at an acute angle with respect to the distal tip 12 and disposed proximal to the distal tip 12 of the electrocautery device at a distance between 3 and 10 mm, thereby providing additional stability to the gas tip. In some embodiments, the second portion is disposed about 3 mm from the distal tip. In some embodiments, the second portion is disposed about 4 mm from the distal tip. In some embodiments, the second portion is disposed about 5 mm from the distal tip. In some embodiments, the second portion is disposed about 6 mm from the distal tip. In some embodiments, the second portion is disposed about 7 mm from the distal tip. In some embodiments, the second portion is disposed about 8 mm from the distal tip. In some embodiments, the second portion is disposed about 9 mm from the distal tip. In some embodiments, the second portion is disposed about 10 mm from the distal tip.

In some embodiments, the second portion is at an angle between 5 and 45 degrees with respect to the distal tip 12. In some embodiments, the outer diameter of the gas tip is less than or equal to the width of the distal tip in order to provide concentrated gas delivery to target structures.

In some embodiments, the gas tip may be formed by overmolding such as by compression molding. The gas tip may be formed from a translucent material to facilitate visualization and reveal potential blockages.

The gas tip 35 is positioned such that, as the gas is delivered, it is dispersed by the electrode's distal tip 12 in a linear pattern and in the direction of adjacent tissue that is not intended for dissection. In certain embodiments, the gas flow is constrained to one side of the gas tip. This adjacent tissue often includes fragile structures, such as vessels and nerves, which are gently pushed away from the electrocautery tip of the electrocautery device while the cauterizing tip maintains solid contact with the tissue. Additionally, when the electrocautery device is used for coagulation, the gas can help clear excessive blood from the surgical area while the blade edge opposite of the gas end maintains solid contact with the bleed site for coagulation as there is no direct gas flow that would inhibit contact. The gas keeps operative tissue relatively dry, increases the operative visibility, prevents char buildup on the blade and reduces the risk of fire in the operative field. Notably, in some embodiments, the gas delivery assembly is configured to deliver any fluid (i.e., a gas and/or a liquid).

The electrocautery device body may be formed by overmolding the device body materials over the insulated electrode 31. In some embodiments, the upper portion 33 and the lower portion 32 of the electrocautery device body are molded as a single unitary piece onto the insulated electrode 31. The electrocautery device body 32 is formed from a non-conductive material (e.g., plastic). In various embodiments, the electrocautery device body comprises one or more materials having properties that are more beneficial for gas delivery than the insulation material, such as a relatively high tensile strength. In certain embodiment, the device body material has a higher flexural modulus as compared to the first insulating material, because threading with a softer material such as an insulating material can allow the threaded gas tube to be over-rotated, resulting in damaged threading on the assembly and an unsecure gas connection. In certain embodiments, the device body material comprises ABS or polycarbonate. Additional valve body material 38 & 38A can be molded to improve the durability of the gas delivery assembly.

Figure 5:
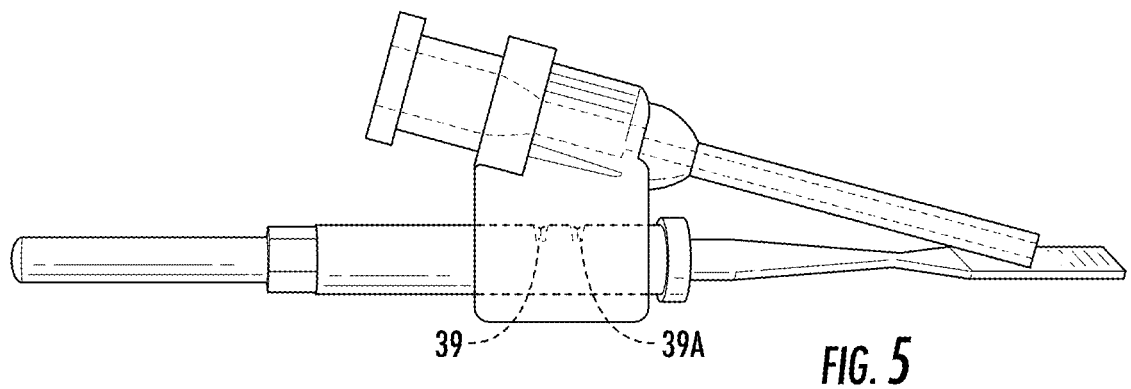
FIG. 5 illustrates an example of the electrocautery device in which a section of the insulation material is recessed to define notches.

With reference to FIG. 5, another embodiment of the electrocautery device is illustrated. As shown in FIG. 5, the insulation material may be recessed to define notches 39 & 39A. This can be used in instances where the electrode insulating material and the material comprising the device body require a mechanical bond instead of a chemical bond.

In some embodiments, the electrocautery device may further comprise a buffer. A typical injection molding process requires that the insulated electrode be placed within a mold cavity with molten plastic. During this process, it is possible that the insulation material will become deformed in response to the high temperature of the molten plastic, resulting in decreased structural integrity. In order to maintain the structure of the insulating material, a buffer may be placed around the insulated electrode to inhibit deformation of the insulation material. The buffer material may include but is not limited to thermoplastics, metals, and wood. The buffer physically constrains the insulation to its current shape and reduces heat transfer to the insulation material on the electrode, helping the electrode insulation retain its structure. The buffer may fully or partially cover the insulation material. In some embodiments, the buffer may have an inner diameter slightly greater than the diameter of the insulating material of the electrode such that the buffer is friction fit with the electrode insulation. In alternative embodiments, the insulated electrode may comprise notches, texturing, and/or other characteristics for inhibiting movement of the buffer.

Figure 6:
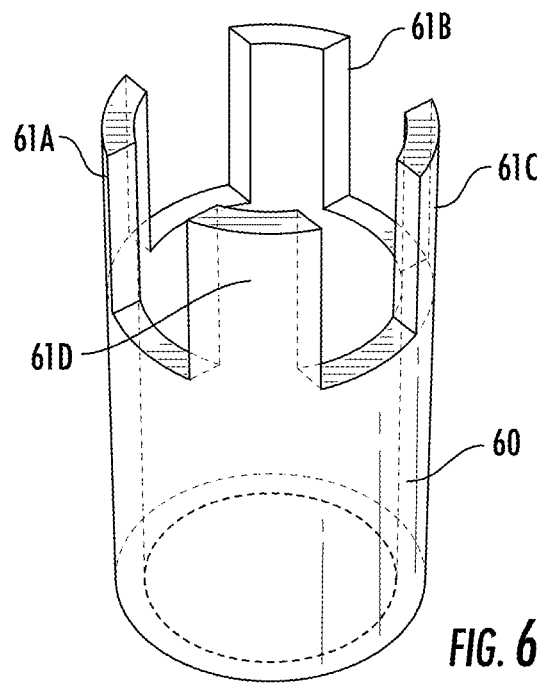
FIG. 6 illustrates a buffer configured for placement around the insulation material.
Figure 7A:
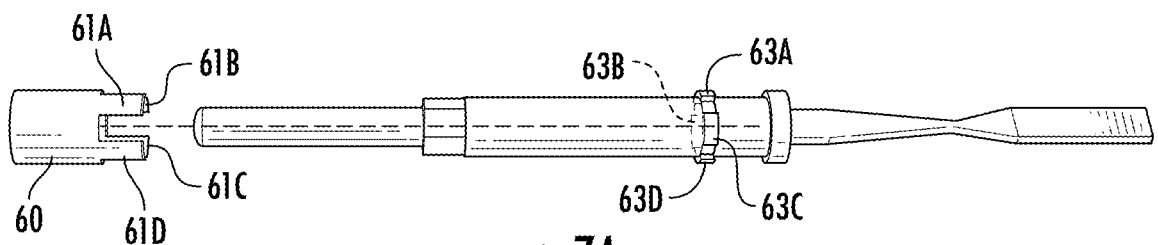
FIG. 7A illustrates an insulated electrode having insulation material shaped to define anti-rotation tabs for connection with a buffer.
Figure 7B:
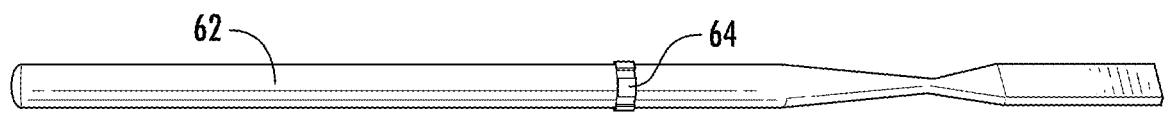
FIG. 7B illustrates an electrode shaped to form the anti-rotation tabs of FIG. 7A.

With reference to the embodiment depicted in FIGS. 6, 7A and 7B, a buffer 60 is depicted. The buffer may have one or more lugs 61A, 61B, 61C, 61D on one or both ends that are configured to couple the buffer to the insulation material of the insulated electrode 62. The insulation material of the insulated electrode may define anti-rotation tabs 63A, 63B, 63C, 63D which, when coupled to the lugs 61A, 61B, 61C, 61D, inhibit movement of the buffer. The electrode 62 may optionally be shaped to partially define the anti-rotation tabs. For example, the electrode may be shaped to include fins 64, as shown in the electrode of FIG. 7B. When the fins 64 are overmolded with an insulation materials, the insulation material will conform to the fins of the electrode, to form the anti-rotation tabs. In alternative embodiments, the electrode may comprise notches, texturing, and/or other characteristics for inhibiting movement of the buffer.

Figure 8:
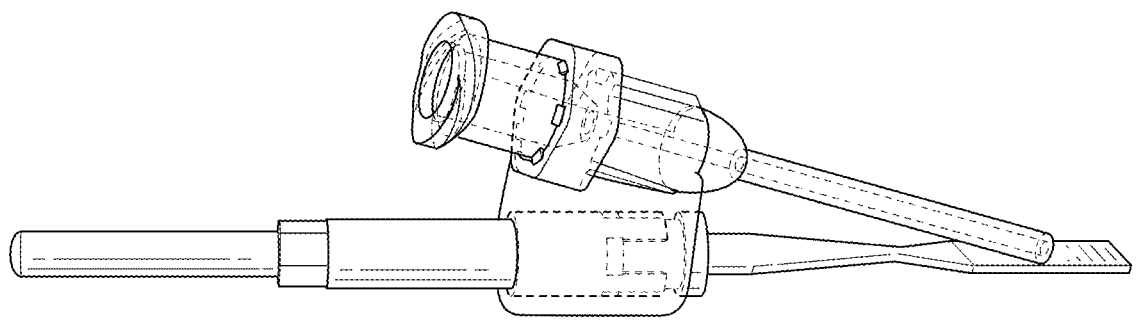
FIG. 8 illustrates an electrocautery device having a buffer disposed around the insulation material.

With reference to FIG. 8, an electrocautery device having a buffer disposed around the insulation material is depicted. The device body material is overmolded onto the insulated electrode and the buffer, forming a mechanical bond between the buffer, insulation, and device body materials.

Figure 9:
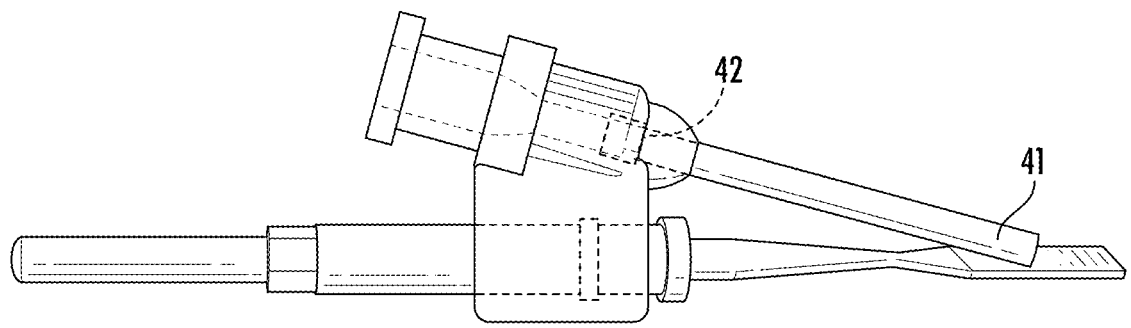
FIG. 9 illustrates an example of the electrocautery device in which the distal end of the gas delivery assembly is formed from a different material.

With reference to FIG. 9, an electrocautery device in which the gas tip 41 is formed from a third material that is distinct from the device body material and the insulation material is depicted. The gas tip 41 is formed by overmolding and is shaped with a neck 42 to enhance the bond between the device body material and the gas tip. In some embodiments, the gas tip has notches on its upper portion. In such embodiments, the notches are held in place by the neck 42, thereby preventing de-coupling of the gas tip from the device body.

Use of a distinct third material to form the gas tip may be advantageous when the properties of the third material (e.g., strength, heat resistance, and/or the like) are preferred over the properties of the device body material. The gas tip may be comprised of a metal, such as stainless steel. In some embodiments, the gas tip may be welded to the distal tip. Optionally, the third material forming the gas tip may be coated with a polymer coating, such as a PTFE coating. In some embodiments, the gas tip 41 is formed by compression molding.

Figure 10:
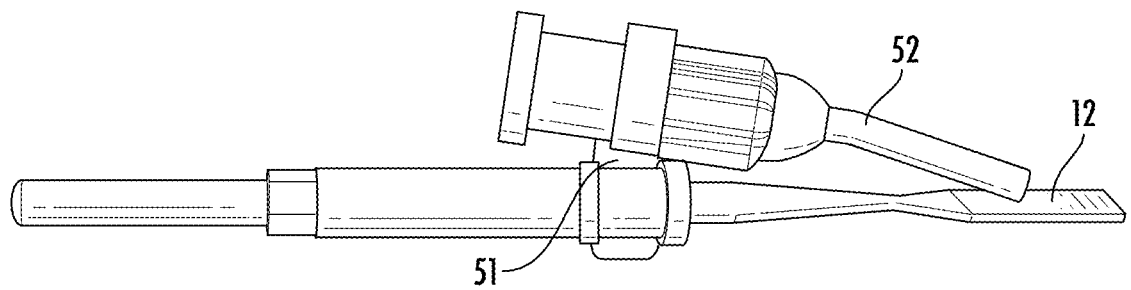
FIG. 10 illustrates an example of the electrocautery device in which the distal end of the gas delivery assembly has been canted.

With reference to FIG. 10, an electrocautery device having a lower profile body 51 is depicted. The distal second portion 52 of the upper portion of the valve body is canted at an angle such that the overall length and height of the gas delivery assembly can be reduced while maintaining the acute angle and distance rearward in relation to the distal tip 12 of the electrode. In various embodiments, the gas delivery channel may extend parallel to the distal tip, with the distal tip 12 of the electrode. In some embodiments, the gas delivery assembly may be canted at an angle to achieve the desired acute angle in relation to the electrocautery blade.

Figure 11:
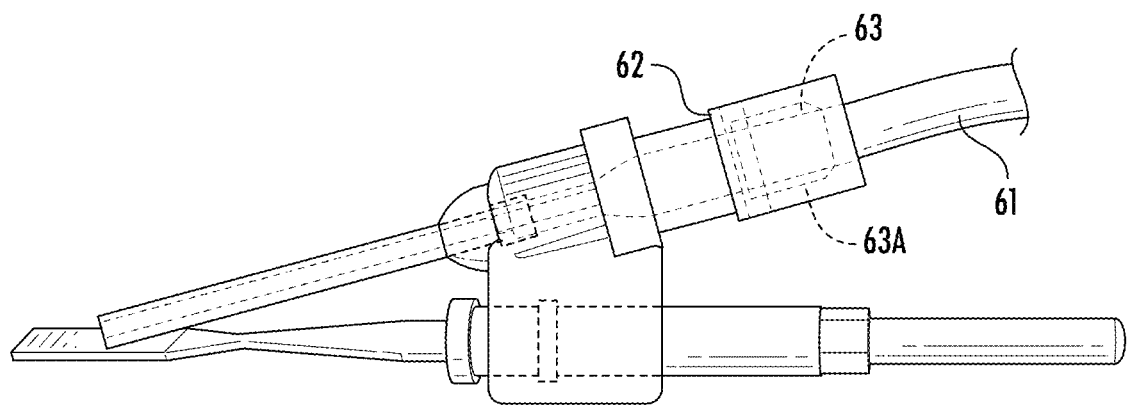
FIG. 11 illustrates an example of the electrocautery device further comprising a gas supply tube.

With reference to FIG. 11, another embodiment of the electrocautery device is depicted in which a gas tube 61 is fluidly coupled to the assembly. The gas tube 61 is overmolded to the assembly, and a catch 62 to hold the gas tube 61 in place and prevent movement when gas is provided from the gas supply source. Fins 63 & 63A are overmolded onto the gas tube to help stabilize the tube within the gas supply connection of the electrocautery device. In some embodiments, the gas tube 61 may be permanently coupled to the electrocautery device. In such embodiments, the gas tube is permanently coupled to the gas supply connection of the electrocautery device via overmolding. In some such embodiments, the gas tube is permanently coupled to the electrocautery device by overmolding one or more materials over at least a portion of the connected portion of the gas tube and gas supply connection. In other embodiments, the gas tube is permanently coupled to the electrocautery device by overmolding the gas tube with the device body material defining the gas supply connection. In other embodiments, the gas tube may be removable. In some embodiments, the gas tube is held in place via friction with a cavity at the gas supply connection.

Figure 12:
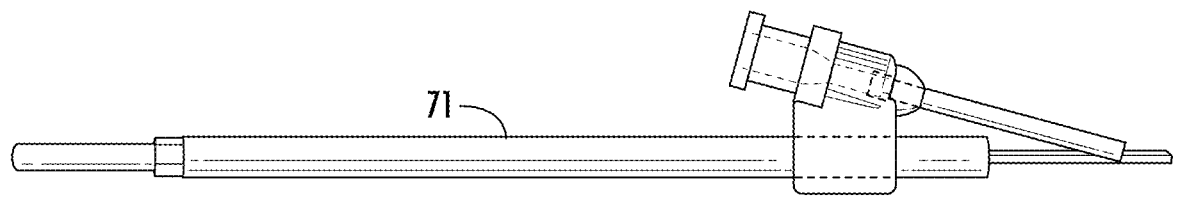
FIG. 12 illustrates an example of the electrocautery device having an extended length.

With reference to FIG. 12, an electrocautery device having an extended length is depicted. In this embodiment, the electrode 71 is elongated and the gas tip of the gas delivery assembly is at an acute angle at a distance that is disposed 3 mm to 10 mm from the distal tip of the electrode of the electrocautery device, in the proximal direction.

Figure 13:
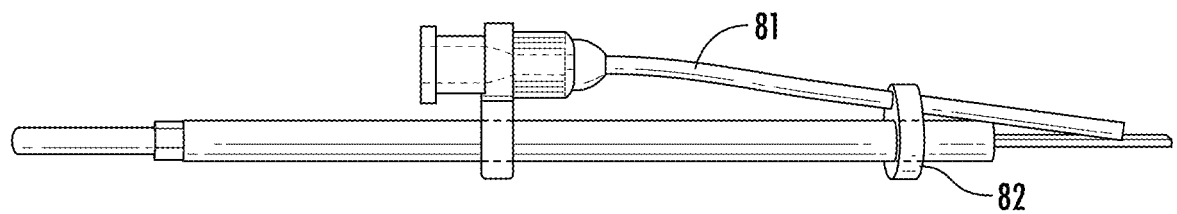
FIG. 13 illustrates an example of the electrocautery device having an extended length and canted distal tip.

With reference to FIG. 13, another embodiment of the electrocautery device having an extended length is depicted. In this embodiment, the upper portion comprises an elongated tube 81 defining the gas delivery channel. The elongated tube 81 is canted to reduce the body size and vertical profile of the electrocautery device. An additional section 82 is overmolded to the elongated tube and the insulation of the electrocautery blade to increase the stability of the elongated tube.

Figure 14:
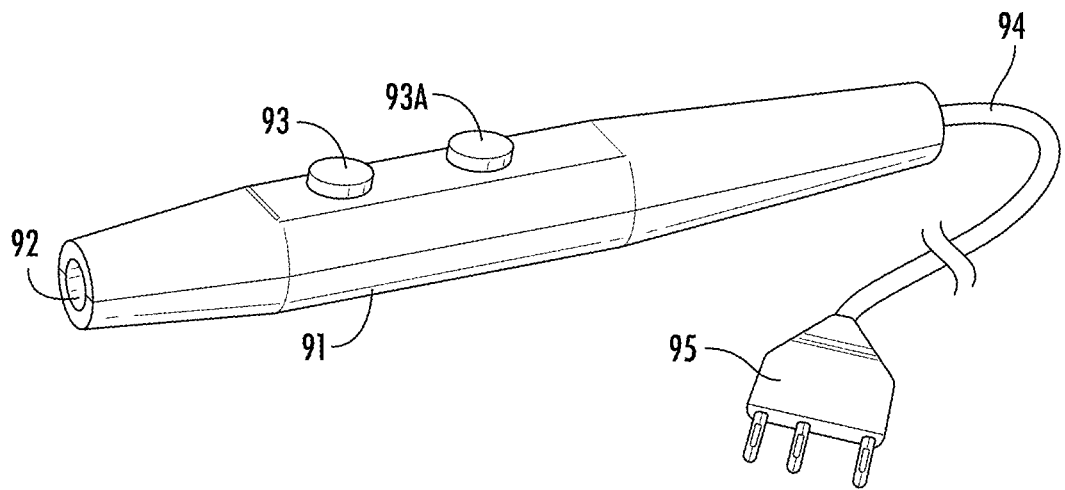
FIG. 14 illustrates an example electrosurgical handpiece for use with the electrocautery device.

With reference to FIG. 14, an isometric view of a electrosurgical handpiece is depicted. The electrosurgical handpiece comprises a housing 91 that is normally gripped by the operator, a slot 92 which internally contains an electrode fastener which holds the electrode, buttons 93 and 93A which control the delivery of current to the electrode, electric wire 94 which is connected to a plug 95 which is intended to connect to an energy supply source such as an electrosurgical generator.

The handpiece allows a user to control the amount of power supplied to the electrode and, ultimately, the biological tissue. The optimal amount of power to be supplied is dependent upon factors such as the size and width of the target tissue, in addition to the desired procedure. The "cutting" mode is typically used for dissecting muscle, subcutaneous fat and fascia or membrane tissue. When the electrocautery device is used in cutting mode, between 40 and 100 watts are applied to the tissue. The "coagulation" mode is typically used to stop bleeding around muscle or subcutaneous fat, but it may also be used for cutting tissue near vessels and nerve bundles and more sensitive fascia or membrane tissue. When the electrocautery device is used in coagulation mode, between 20 and 60 watts are applied to the tissue.

Figure 15:
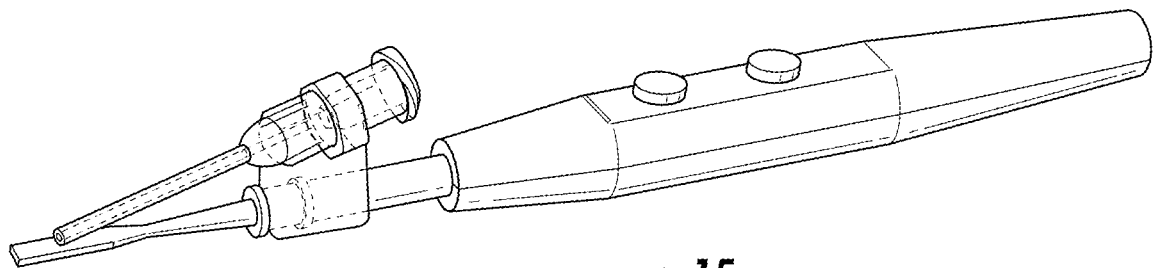
FIG. 15 illustrates an example of the electrocautery device coupled to an electrosurgical handpiece.

With reference to FIG. 15, the electrocautery device coupled with an electrosurgical handpiece is depicted. The lower portion of the electrocautery device body is coupled to a slot in the electrosurgical handpiece and held in place by an internal electrode fastener within the handpiece. The overmolded electrode with gas delivery assembly may be rotated in relation to the handpiece.

Figure 16:
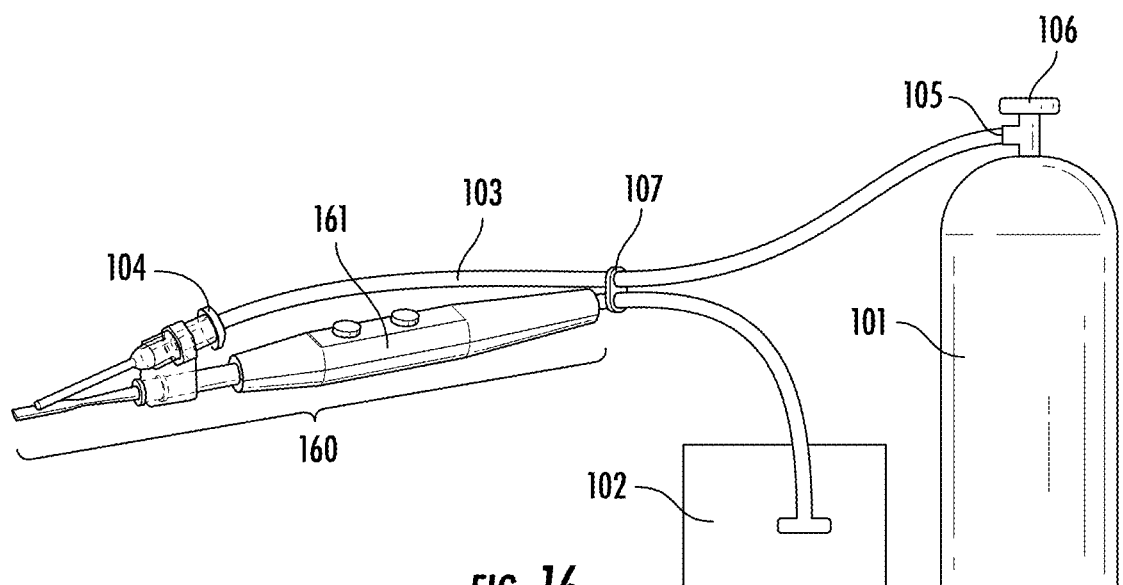
FIG. 16 illustrates an example of the system for dissecting biological tissue.

With reference to FIG. 16, the system for dissection of biological tissue is depicted. The system comprises an electrocautery device 160, a gas supply source 101 coupled to a gas supply of the electrocautery device via a gas supply tube 103, an energy supply source 102 configured to deliver an electrical current to the electrode of the electrocautery device, and a handpiece 161 that is operably coupled to the energy supply source.

At a first end, the gas supply tube 103 connects to the electrocautery device 104 via the gas supply connection of the electrocautery device. At a second end, the gas supply tube 103 connects to a nozzle 105 on the gas source. In various embodiments, the gas supply tube is fluidly connected to one or both of the electrocautery device 104 and gas source nozzle 105 via threaded adapters. A valve on the gas source 106 is used to control the flow of gas to the electrocautery blade.

The gas supply source may be a gas tank or other feed such as a box or regulator. Alternatively, the gas supply source may be a direct gas line. Alternative gas control systems may be used. Examples of such alternative gas control systems include a foot pedal valve control, a remote valve located next to the user of the electrocautery device, as well as any other gas control system. In some embodiments, the gas supplied by the gas supply source is an inert gas. In some such embodiments, the gas is carbon dioxide. In other embodiments, the gas supplied by the gas supply source is argon.

The gas tube and gas supply source are not coupled to the energy supply source. Decoupling of the gas supply source and the energy supply source isolates damage caused by failure of either system. A coupler 107 is attached to the gas tube and the electric wire to keep the system organized and avoid potential injury to the use or damage to the system.

In some embodiments, the entirety of the gas supply source and gas tube is external to the handpiece and visible to the operator. This allows for the identification of potential blockages or damage to the gas system.

There have been illustrated and described various embodiments of an overmolded electrocautery blade with gas delivery assembly. The features of the several embodiments described herein may be combined without limitation.

Modifications of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An electrocautery device for dissecting biological tissue, the electrocautery device comprising:
   an insulated electrode, the insulated electrode comprising:
      an electrode having a distal tip configured to deliver an electrical current to a biological tissue and a proximal end configured to be coupled to an energy supply source; and
      an insulation material radially disposed on a middle portion of the electrode such that the distal tip and the proximal end of the electrode is not covered by the insulation material,
   an electrocautery device body formed from a device body material, the electrocautery device body comprising:
      a lower portion radially disposed upon the insulated electrode; and
      an upper portion formed as a single unitary piece with the lower portion, wherein the upper portion defines a gas delivery assembly comprising:
         a first portion formed at the proximal end of the upper portion, the first portion comprising a gas supply connection, wherein the gas supply connection is configured to receive gas from a gas supply source; and
         a second portion distal to the first portion, the second portion defining a gas delivery channel; and
      a gas tip coupled to and extending distally from a distal end of the second portion;
   wherein the gas delivery channel is in fluid communication with the gas supply connection such that, when the gas supply source is coupled to the gas supply connection, the gas delivery channel is configured to deliver a gas provided by the gas supply source to the biological tissue via the gas tip.

2. The electrocautery device of claim 1, wherein the insulated electrode is formed by overmolding the insulation material onto a middle portion of the electrode.

3. The electrocautery device of claim 2, wherein the insulation material is overmolded onto the middle portion of the electrode by injection molding.

4. The electrocautery device of claim 1, wherein the electrocautery device body is formed by overmolding the device body material onto the insulated electrode.

5. The electrocautery device of claim 1, wherein the insulation material is overmolded onto the middle portion of the electrode by compression molding.

6. The electrocautery device of claim 1, wherein the distal tip is shaped as a blade.

7. The electrocautery device of claim 1, wherein the gas supply connection comprises a threaded connection.

8. The electrocautery device of claim 1, wherein the gas supply connection comprises a tapered connection configured to facilitate a friction fit between the gas supply source and the gas supply connection.

9. The electrocautery device of claim 1, wherein the insulated electrode further comprises a buffer disposed on an external surface of the insulation material and configured to mitigate or prevent deformation of the insulation material.

10. The electrocautery device of claim 9, wherein:
the buffer comprises one or more lugs on at least one end of the buffer;
the insulation material comprises anti-rotation tabs; and
the lugs and the anti-rotation tabs are configured to interact such that the buffer is held in place by the anti-rotation tabs.

11. The electrocautery device of claim 10, wherein the anti-rotation tabs of the insulation material are defined by the shape of the insulated electrode.

12. The electrocautery device of claim 1:
wherein the proximal end of the electrode is configured to be coupled to a handpiece, the handpiece being operably coupled to the energy supply source; and
wherein the handpiece is configured to, when manipulated by a user, increase or decrease an amount of power provided to the electrocautery device by the electrical current.

13. The electrocautery device of claim 1, wherein the gas tip is formed from a third material that is distinct from the insulation material and the device body material.

14. The electrocautery device of claim 1, wherein the gas tip is disposed adjacent to the distal tip of the insulated electrode.

15. The electrocautery device of claim 1, wherein the second portion of the upper portion of the electrocautery device body and the lower portion of the electrocautery device body form an acute angle.

16. The electrocautery device of claim 1, wherein the second portion of the upper portion of the electrocautery device body and the lower portion of the electrocautery device body is canted such that the angle between its proximal end and the lower portion of the device body is less than the angle between its distal end and the lower portion of the device body.

17. The electrocautery device of claim 1, wherein the second portion of the upper portion of the electrocautery device body and the lower portion of the electrocautery device body is canted such that the angle between its proximal end and the lower portion of the device body is greater than the angle between its distal end and the lower portion of the device body.

18. A system for dissecting biological tissue, the system comprising:
an electrocautery device, the electrocautery device comprising:
an insulated electrode, the insulated electrode comprising:
an electrode having a distal tip configured to deliver an electrical current to a biological tissue and a proximal end configured to be coupled to an energy supply source; and
an insulation material radially disposed on a middle portion of the electrode such that the distal tip and the proximal end of the electrode is not covered by the insulation material, and
an electrocautery device body, the electrocautery device body comprising:
a lower portion radially disposed upon the insulated electrode; and
an upper portion formed as a single unitary piece with the lower portion, wherein the upper portion defines a gas delivery assembly comprising:
a first portion formed at the proximal end of the upper portion, the first portion comprising a gas supply connection, wherein the gas supply connection is configured to be coupled to a gas supply source; and
a second portion distal to the first portion, the second portion defining a gas delivery channel; and
a gas tip coupled to and extending distally from a distal end of the second portion;
wherein the gas delivery channel is in fluid communication with the gas supply connection such that, when the gas supply source is coupled to the gas supply connection, the gas delivery channel is configured to deliver a gas provided by the gas supply source to the biological tissue via the gas tip of the electrocautery device,
a gas supply source coupled to the gas supply connection of the electrocautery device via a gas supply tube;
an energy supply source configured to deliver an electrical current to the electrode of the electrocautery device; and
a handpiece operably coupled to the energy supply source, wherein the handpiece is configured to, when manipulated by a user, increase or decrease an amount of power provided to the electrocautery device by the electrical current.

19. The system of claim 18, further comprising a gas pump operably coupled to a proximal end of the gas tube and configured to facilitate movement of a gas from the gas source to the gas delivery assembly of the electrocautery device.

20. The system of claim 18, wherein the gas supply tube is permanently coupled to the gas supply connection of the electrocautery device via overmolding.

* * * * *